(12) United States Patent
Brown

(10) Patent No.: US 6,204,405 B1
(45) Date of Patent: Mar. 20, 2001

(54) ECONOMICAL AND CONVENIENT PROCEDURES FOR THE SYNTHESIS OF CATECHOLBORANE

(75) Inventor: Herbert C. Brown, West Lafayette, IN (US)

(73) Assignee: Sigma-Aldrich Co.

( * ) Notice: Subject to any disclaimer, the term of this patent is extended or adjusted under 35 U.S.C. 154(b) by 0 days.

(21) Appl. No.: 09/469,274

(22) Filed: Dec. 22, 1999

(51) Int. Cl.[7] .................................................. C07F 5/04
(52) U.S. Cl. ................................................................ 558/288
(58) Field of Search ................................................ 558/288

(56) References Cited

U.S. PATENT DOCUMENTS 4,739,096 * 4/1988 Noth et al. ............................ 558/288
5,973,185 * 10/1999 Ma et al. ............................... 558/288

* cited by examiner

*Primary Examiner*—Deborah C. Lambkin

(57) ABSTRACT

New, economical and convenient procedures for the preparation of catecholborane in high chemically pure form using tri-O-phenylene bis borate readily prepared from the reaction of catechol with boric acid, and diborane or borane-Lewis base complexes.

8 Claims, No Drawings

ECONOMICAL AND CONVENIENT PROCEDURES FOR THE SYNTHESIS OF CATECHOLBORANE

This invention relates to new, economical and convenient procedures for the preparation of catecholborane. These processes provide catecholborane in high yields and chemically pure form.

PRIOR ART

Catecholborane is one of the most versatile boron hydride reagents available for synthetic chemists. It has found a multitude of applications as a selective reducing and hydroborating agent (Brown, H. C.; Gupta, S. K. *J. Am Chem. Soc.,* 1971, 93, 1816. Brown, H. C.; Gupta. S. K. *J. Am Chem. Soc.,* 1971, 93, 4062. Lane, C. F.; Kabalka, G. W. *Tetrahedron* 1976, 32, 981. Kabalka, G. W. Org. *Prep. Proc. Intl.,* 1977, 9, 133. Kabalka, G. W.; Baker, Jr., J. D.; Neal, G. W. *J. Org. Chem.,* 1977, 42, 512. VanNieuwenhze, M. S. *Encyclopedia of Reagents for Organic Synthesis;* Wiley: New York, vol. 2, Ed. Paquette, L. A., 1995, p1017. Brown, H. C. *Organic Synthesis via Boranes;* Aldrich Chemical Co., Inc.; Milwaukee, Wis., 1997; Vol. 1.). It has been effectively used in the preparation of alkyl- and alkenylboronic acids (Brown, H. C.; Gupta, S. K. *J. Am Chem. Soc.,* 1972, 94, 4370. Brown, H. C.; Gupta, S. K. *J. Am Chem. Soc.,* 1975, 73, 5249. Brown, H. C.; Chandrasekhran, J. *J. Org. Chem.,* 1983, 48, 5080). Particularly its usage in conjunction with chiral oxazaborolidine and chiral transition-metal complex catalysts provides a unique tool for the synthesis of chiral alcohols in very high enantioselectivities (Mannig, D; Noth, H. *Angew. Chem., Int. Ed. Engl.,* 1985, 24, 878. Burgess, K.; Ohlmeyer, M. J. *Chem. Rev.,* 1991, 91, 1179. Corcy, E. J.; Helal, C. J. *Angew. Chem., Int. Ed. Engl.,* 1998, 37, 1986).

Though catecholborane can be prepared by other procedures (Newson, H. C.; Woods, W. G. *Inorg. Chem.,* 1968, 7, 177. Suseela, Y.; Periasamy, M. *J. Organomet. Chem.,* 1993, 450, 47), the most preferred way of preparation is by the reaction of catechol with borane-tetrahydrofuran or borane-methyl sulfide (eq. 1) (Brown, H. C.; Gupta, S. K. *J. Am Chem. Soc.,* 1971, 93, 1816. Brown, H. C.; Mandal, A. K.; Kulkarni, S. U. *J. Org. Chem.,* 1977, 42, 1392).

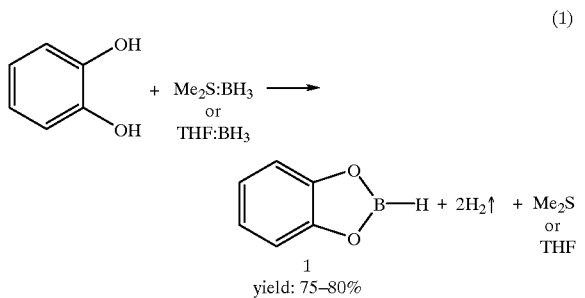

(1)

yield: 75–80%

The product catecholborane was isolated by distillation (bp 50° C./50 mmHg). The catecholborane thus obtained is moisture sensitive, but is stable in dry air and can be stored at 0° C. for long periods. However, this procedure does suffer from some disadvantages, such as the waste of two equivalents of active hydrides and the liberation of large amounts of hydrogen, which may be of concern in large-scale applications. Also, the commercially available catecholborane contains considerable amounts of borate impurities. On the other hand, the increasing use of catecholborane in materials and medicinal chemistries warrants more economic and convenient options for the synthesis of this important borane reagent, with increased chemical purity. The present invention provides new, economical and convenient procedures for the preparation of catecholborane.

SUMMARY OF THE DISCLOSURE

New, economical and convenient procedures for the preparation of catecholborane in high chemical pure form using tri-O-phenylene bis borate, readily prepared from the reaction of catechol with boric acid, and diborane or borane-Lewis base complexes. This procedure utilizes only one molar equivalent of a boron-hydrogen bond per mole of catecholborane, instead of the three molar equivalents of boron-hydrogen bonds required by the present procedure. As used herein, the following terms have the following meanings:

"Borate 2" stands for tri-O-phenylene bis borate.

"Cyclic ethers" refers to ethers, such as tetrahydrofuran, tetrahydrofuran, dioxane and the like.

"Organic sulfides" refers to compounds such as dimethyl sulfide, diisoamyl sulfide and thioxane.

"Tertiary amines" refers to amines such as triethylamine, tert-butyldiethylamine, N,N-dimethylaniline and N-ethyl-N-isopropylaniline.

"Halogenated hydrocarbons" include both aliphatic and aromatic such as dichloromethane, 1,2-dichloroethane and chlorobenzene.

"Hydrocarbon solvents" include both aliphatic and aromatic such as n-heptane, toluene and tetralin, with boiling points in the range of 50–300° C.

"RB" refers to a round-bottom flask.

As mentioned in the prior art, the current popular preparation of catecholborane using the reaction of catechol with borane-methyl sulfide involves the wastage of two equivalents of active hydride. Also, the resulting excess evolution of hydrogen makes this process somewhat disadvantageous for large-scale preparations. In order to reduce the cost of catecholborane preparation and to avoid the formation of hydrogen gas side product, a modified synthesis of catecholborane was envisioned through the exchange of >B—H of diborane to >B—O— of tri-O-phenylene bis borate (hereafter called "borate 2"). This was examined according to the following equation.

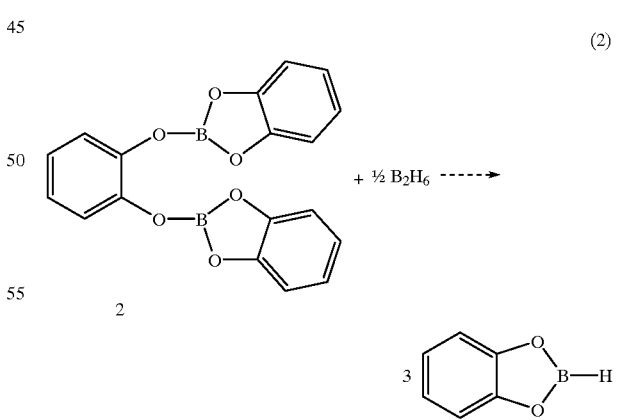

(2)

The borate 2 can be conveniently prepared from inexpensive catechol and boric acid according to the reported procedures (Thomas, L. H. *J. Chem. Soc.,* 1946, 820. Gerrard, W.; Lappert, M. F.; Mountfield, B. A. *J. Chem Soc.,* 1959, 1529. Mehrotra, R. C.; Srivastava, G. *J. Chem Soc.,* 1961, 4046).

Initially, the synthesis of catecholborane was attempted by the reaction of borate 2 (white solid, mp 102° C.) with diborane at room temperature. However, the reaction proceeds very slowly at room temperature, but the exchange was greatly accelerated at higher temperatures. The reaction proceeds very rapidly at 102° C., at which temperature the borate 2 melts and catecholborane was obtained in 80% yield after distillation. However, diborane gas is sensitive to high temperatures in the absence of Lewis bases and may result in unwanted higher boranes. This problem was addressed by using an inert solvent that dissolves borate 2 and does not interfere with the isolation procedure for catecholborane.

Accordingly, the borate 2 was taken in toluene and diborane gas was bubbled into this solution. The progress of the reaction was followed by $^{11}$B NMR examination of the reaction mixture. Here also, the reaction of borate 2 with diborane is very slow at room temperature. It was greatly accelerated at higher temperatures (90–100° C.) and catecholborane was obtained in 85% yield $^{11}$B NMR, +28.2 ppm, d). The reaction temperatures could be brought down considerably by performing the reaction in glymes, such as di-, tri-, or tetraglymes, in which borate 2 is somewhat soluble. Thus the borate 2 was taken in tetraglyme and diborane gas was passed into this mixture. The diborane gas readily reacts with the tetraglyme solution of borate 2 at 70° C., and catecholborane was formed in 85% yield and 15% of unreacted borate 2 was also observed (by $^{11}$B NMR, +22.3 ppm). The catecholborane thus obtained was distilled out from tetraglyme conveniently in 83% yield with 98% chemical purity (by $^{11}$B NMR, +28.2 ppm, d). The $^{11}$B NMR examination of the residual tetraglyme showed only the presence of unreacted borate 2 (15%). To this tetraglyme solution, additional borate 2 (85%) can be added and treated with diborane (Scheme 1). This provides an ideal procedure for the synthesis of catecholborane.

Fhus, heating the borate 2 with borane-methyl sulfide in toluene to 100° C. (bath temperature) for 3 h provides clean catecholborane. The $^{11}$B NMR showed the disappearance of the peak due to BMS at −20.2 ppm and the appearance of a new peak due to catecholborane at +28.2 ppm (doublet). It also showed some (10%) starting borate 2. This may be due to some loss of borane due to the higher reaction temperature. Using a small excess of Me$_2$S:BH$_3$ reduces the amount of unreacted borate 2, however, it could not be removed completely. However, the catecholborane prepared in this way was of better purity than the present commercial sample as observed by $^{11}$B NMR.

In order to carry out the reaction at lower temperatures, the reaction was also tried in dichloromethane. Borane-methyl sulfide complex was added to the borate 2 in dichloromethane and the contents were stirred further. Here also the equilibration was slow at room temperature. It was accelerated considerably under reflux conditions. however, in dichloromethane, even under reflux conditions, the equilibration reaction required 48 h for the predominant formation of catecholborane.

(3)

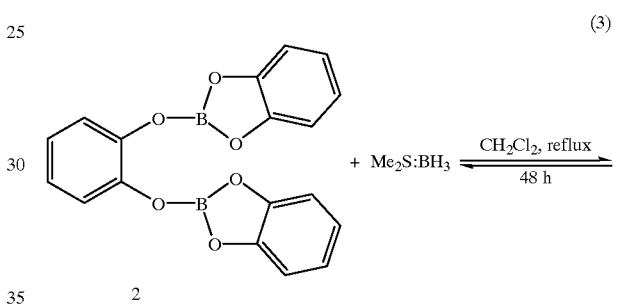

Scheme 1

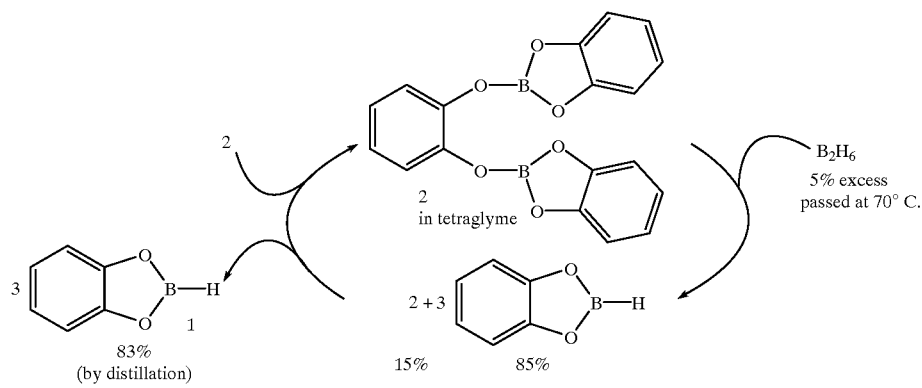

The other glymes, such as diglyme, and triglyme, also give comparable results and preparation of catecholborane was carried out without problems with the isolation of catecholborane. However, monoglyme, a low boiling glyme has a boiling point close to that of catecholborane which complicates the isolation of catecholborane.

Further, this exchange of >B—H of borane to >B—O— of tri-O-phenylene bis borate can be also affected by using borane-Lewis bases as >B—H source, in solvents that are inert to borane and catecholborane.

-continued

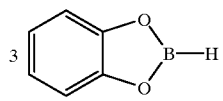

Catecholborane was also prepared from the borate 2 and Me$_2$S:BH$_3$ in other solvents such as tetrahydrofuran, n-heptane and in neat conditions. Table 1 summarizes the results.

In order to obtain neat catecholborane, the solvent used as reaction medium needs to be separated from the reaction mixture in all these procedures. Unfortunately, in the case of high boiling solvents, such as toluene, n-heptane and THF, considerable amounts of mixtures were obtained, since the boiling point of catecholborane is relatively low (bp 77° C./100 mmHg). This problem was circumvented by treating the borate 2 with $Me_2S:BH_3$ without any solvent and heating the reaction mixture slowly to 102° C., at which temperature the borate 2 melts and the dimethyl sulfide distills and is recovered. However, under these conditions a small amount of diborane gas escapes. Accordingly, a small excess (2–4%) of $Me_2S:BH_3$ is recommended. It is of interest to note that attempts to use a similar neat reaction with catechol and $Me_2S:BH_3$ gave poor results earlier (Brown, H. C.; Mandal, A. K.; Kulkarni, S. U. *J. Org. Chem.*, 1977, 42, 1392). Apparently, borate 2 is more convenient for such preparations.

TABLE 1

Preparation of Catecholborane[a] from Borate 2 and $Me_2S:BH_3$.

| Reaction Solvent | Reaction Conditions |
| --- | --- |
| Toluene | 90° C./4h |
| Toluene | 110° C./2h |
| Dichloromethane | Reflux/48h |
| Tetrahydrofuran | Reflux/12h |
| n-Heptane | Reflux/10h |
| Neat (no solvent) | 102° C./2h |

[a]Borate 2 (10 mmol) was added to the solvent, $Me_2S:BH_3$ (11 mmol) added, and the contents were slowly heated to the conditions mentioned above. The completion of catecholborane formation was established by $^{11}B$ NMR analysis.

The catecholborane was also prepared using the borate 2 with other reactive borane-Lewis base complexes such as $THF:BH_3$, $i-Am_2S:BH_3$, $PhEtPr^iN:BH_3$, $PhEt_2N:BH_3$, $i-Pr_2Bu^iN:BH_3$ $Et_3N:BH_3$ and $i-Pr_2EtN:BH_3$ following the procedures similar to that used for borate 2 and $Me_2S:BH_3$. Borane-tetrahydrofuran readily reacts with borate 2 even at room temperature and the catecholborane was obtained in 80% yield after the removal of volatile tetrahydrofuran. With the amine-borane complexes, the initial equilibration with borate 2 readily occurs at room temperature. However, the liberated amine from the amine-borane after this initial reaction complexes with the borate 2, as observed by the $^{11}B$ NMR examination, which showed peaks corresponding to the formation of amine complexes of borate 2 and this requires additional heating to achieve further reaction.

The catecholborane thus obtained after distillation can be stored at 0° C. and no appreciable disproportionation was noted. However, when stored at room temperature the amount of borate seems to increase, similar to the observations made earlier (Lane, C. F.; Kabalka, G. W. *Tetrahedron* 1976, 32, 981).

DETAILED DESCRIPTION OF PREFERRED EMBODIMENTS

The following examples further illustrate the present invention. All manipulations and reactions with air-sensitive compounds were carried out in an inert atmosphere (dry nitrogen, argon etc). The special techniques employed in handling air-sensitive materials are described elsewhere (Brown, H. C. *Organic Synthesis via Boranes;* Aldrich Chemical Co., Inc.; Milwaukee. Wis., 1997; Vol. 1). All the glassware was oven-dried for several hours, assembled while hot, and cooled in a stream of dry nitrogen gas. $^{11}B$ NMR spectra were recorded on a Varian-Gemini 300 MHz multinuclear instrument. The chemical shifts δ are in ppm relative to $BF_3:OEt_2$. Hydride analysis studies were carried out using the gasimeter. Triglyme and tetraglyme (anhydrous), catechol, $Me_2S:BH_3$ were procured from Aldrich, boric acid (Mallinckrodt), were used as obtained. All the solvents, toluene, n-heptane, THF, and dichloromethane were distilled prior to use.

Preparation of tri-O-phenylene bis borate (2)

This was prepared closely following the literature procedure (Gerrard, W.; Lappert, M. F.; Mountfield, B. A. *J. Chem Soc.,* 1959, 1529). An oven-dried RB flask provided with a septum inlet and a stirring bar fitted with Dean-Stark apparatus was charged with catechol (16.52 g, 150 mmol) and boric acid (6.18 g, 50 mmol) in toluene (50 mL). The contents were gently refluxed till all of $H_2O$ (5.4 g, 300 mmol), formed during the reaction had been collected in the Dean-Stark apparatus (~3–4 h). The completion of reaction was also confirmed by $^{11}B$ NMR, which showed clean formation of borate 2 (+22.3 ppm, s), with no other boron species present. The solvent toluene was distilled-out to obtain borate 2 as a white solid (mp: 99–102° C., lit. 97–103° C.) in quantitative yields.

EXAMPLE 1

Preparation of catecholborane from the borate 2 and diborane gas

An oven-dried RB flask provided with a septum inlet, stirring bar and gas bubbler was assembled hot and cooled to room temperature under a stream of nitrogen. The gas bubbler was connected to a diborane generation set-up as described elsewhere. The flask was charged with the borate 2 (17.31 g, 50 mmol) in a temperature bath that was kept at 100° C. Diborane gas (40 mmol, excess), generated as described elsewhere, (Brown, H. C. *Organic Synthesis via Boranes;* Aldrich Chemical Co., Inc.; Milwaukee, Wis., 1997; Vol. 1, Kanth, J. V. B.; Brown, H. C. manuscript in preparation) was passed into the reaction mixture slowly. The diborane gas was readily reacted with the borate 2. The $^{11}B$ NMR examination showed clean formation of catecholborane in addition to a minor amount of unreacted borate 2 (10%). After the complete generation and absorption of diborane gas, the gas bubbler was removed and the reaction flask was fitted with a distillation set-up. Distillation under reduced pressure (49° C./50 mmHg, lit. 50° C./50 mmHg, VanNieuwenhze, M. S. *Encyclopedia of Reagents for Organic Synthesis;* Wiley: New York, vol. 2, Ed. Paquette, L. A., 1995, p1017) provided catecholborane in 80% yield (12.83 g) and in 98% chemical purity. The residue in the distillation flask was identified as the borate 2, which can be mixed with further amounts of borate 2 and used again for the generation of catecholborane.

EXAMPLE 2

Preparation of catecholborane from the borate 2 and diborane gas in toluene

The procedure followed for all solvents, such as toluene, n-heptane, tetralin, diphenyl ether, etc., was essentially the same and the procedure followed using tetraglyme as solvent is representative.

An oven-dried RB flask provided with a septum inlet, stirring bar and gas bubbler was assembled hot and cooled to room temperature under a stream of nitrogen. The gas bubbler was connected to a diborane generation set-up as described elsewhere. The flask was charged with the borate 2 (17.31 g, 50 mmol) in dry toluene (30 ml,) and the reaction mixture was kept at 90° C. (bath temperature). Diborane gas (40 mmol, excess), generated as described elsewhere, (Brown, H. C. *Organic Synthes via Boranes;* Aldrich Chemical Co., Inc.; Milwaukee, Wis., 1997; Vol. 1, Kanth, J. V. B.; Brown, H. C. manuscript in preparation) was passed into the reaction mixture slowly, during 4 h. The diborane gas was slowly absorbed into the borate-tetraglyme mixture. The $^{11}$B NMR examination showed clean formation of the catecholborane in 86% yield in addition to a minor amount of unreacted borate 2 (14%).

EXAMPLE 3

Preparation of catecholborane from the borate 2 and diborane gas in a glyme

The procedure followed in the glymes such as di-, tri-, and tetraglyme, was essentially the same and the procedure followed using tetraglyme as solvent is representative.

An oven-dried RB flask provided with a septum inlet, stirring bar and gas bubbler was assembled hot and cooled to room temperature under a stream of nitrogen. The gas bubbler was connected to a diborane generation set-up as described elsewhere. The flask was charged with the borate 2 (17.31 g, 50 mmol) in dry tetraglyme (30 mL) and the reaction mixture was kept at 70° C. Diborane gas (30 mmol, small excess), generated as described elsewhere. (Brown, H. C. *Organic Synthesis via Boranes;* Aldrich Chemical Co., Inc.; Milwaukee, Wis., 1997; Vol. 1, Kanth, J. V. B.; Brown, H. C. manuscript in preparation) was passed into the reaction mixture slowly. The diborane gas was readily absorbed into the borate-tetraglyme mixture. The $^{11}$B NMR examination showed clean formation of catecholborane in addition to a minor amount of unreacted borate 2 (10%). After the complete generation and absorption of diborane gas, the gas bubbler was removed and the reaction flask was fitted with a distillation set-up. Distillation under reduced pressure provided catecholborane in 83% yield (13.32 g) and in 98% chemical purity. The residue in the distillation flask was identified as the borate 2 in tetraglyme, which can be mixed with further amounts of borate 2 and used again for the generation of catecholborane.

EXAMPLE 4

Preparation of catecholborane from the borate 2 and borane-Lewis base complex without solvent The procedure followed with all the borane-Lewis base complexes, wherein the Lewis base could an amine, cyclic ether or dialkyl sulfide, is essentially same. The following procedures are representative.

An oven-dried RB flask provided with a septum inlet, stirring bar and a reflux condenser was assembled hot and cooled to room temperature under a stream of nitrogen. The flask was charged with the borate 2 (17.31 g, 50 mmol) and borane-methyl sulfide (5.0 mL, 10.2 M, 51 mmol). The reaction mixture was slowly heated to 100° C. for 1 h, by which time the $^{11}$B NMR examination showed the disappearance of the peak due to borane-methyl sulfide complex (−20.2 ppm, q) and the appearance of a new peak due to catecholborane (+28.3 ppm, d). The methyl sulfide liberated, was pumped-off and the residue was distilled under reduced pressure to obtain catecholborane in 85% yield (13.64 g) and 97% chemical purity.

EXAMPLE 5

Preparation of catecholborane from the borate 2 and borane-triethylamine complex An oven-dried RB flask provided with a septum inlet, stirring bar and a reflux condenser was assembled hot and cooled to room temperature under a stream of nitrogen. The flask was charged with the borate 2 (17.31 g, 50 mmol) and borane-triethylamine complex (5.86 g, 51 mmol) was added at room temperature. The reaction mixture was slowly heated to 70° C. for 1 h, by which time the $^{11}$B NMR examination showed the disappearance of the peak due to borane-triethylamine (−12.8 ppm, q) and the appearance of a new peak due to catecholborane (+28.3 ppm, d). The triethylamine liberated, was pumped-off and the residue was distilled under reduced pressure to obtain catecholborane in 70% yield (11.23 g) and 96% chemical purity.

EXAMPLE 6

Preparation of catecholborane from the borate 2 and borane-N-ethyl-N-isopropylaniline complex An oven-dried RB flask provided with a septum inlet, stirring bar and a reflux condenser was assembled hot and cooled to room temperature under a stream of nitrogen. The flask was charged with the borate 2 (17.31 g, 50 mmol) and borane-N-ethyl-N-isopropylaniline complex (10.2 mL, 5.0 M, 51 mmol) was added at room temperature. The reaction mixture was slowly heated to 70° C. for 1 h, by which time the $^{11}$B NMR examination showed the disappearance of the peak due to borane-N-ethyl-N-isopropylaniline (−14.5 ppm, q) and the appearance of a new peak due to catecholborane (+28.3 ppm, d). As the boiling point of N-ethyl-N-isopropylaniline (50° C./1 mmHg) is much higher than that of catecholborane, distillation under reduced pressure yielded catecholborane in 83% yield (13.31 g) and 96% chemical purity.

EXAMPLE 7

Preparation of catecholborane from the borate 2 and borane-isoamyl sulfide complex An oven-dried RB flask provided with a septum inlet, stirring bar and a reflux condenser was assembled hot and cooled to room temperature under a stream of nitrogen. The flask was charged with the borate 2 (17.31 g, 50 mmol) and borane-isoamyl sulfide complex (12.7 mL, 4.0 M, 51 mmol) was added at room temperature. The reaction mixture was slowly heated to 70° C. for 1 h, by which time the $^{11}$B NMR examination showed the disappearance of the peak due to borane-isoamyl sulfide (−23.2 ppm, q) and the appearance of a new peak due to catecholborane (+28.3 ppm, d). Distillation under reduced pressure yielded catecholborane in 80% yield (12.89 g) and 97% chemical purity.

EXAMPLE 8

Preparation of catecholborane from borate 2 and THF:BH$_3$

An oven-dried RB flask provided with a septum inlet, stirring bar and a reflux condenser was assembled hot and cooled to room temperature under a stream of nitrogen. The flask was charged with the borate 2 (17.31 g, 50 mmol), followed by THF:BH$_3$ (51 mL, 1.0 M, 51 mmol). The progress of the reaction was followed by $^{11}$B NMR analysis of the reaction mixture. Initially, the reaction mixture was stirred at room temperature for 2 h, by which time 80% of the reaction is complete. The contents were then slowly heated to 50° C. (bath temperature) maintaining a constant pressure of dry nitrogen. It showed the disappearance of the peak due to the borane-THF complex (−0.2 ppm, q) and the appearance of a new peak due to catecholborane (+28.3 ppm, d, ~90%). The reaction mixture also showed some amount of unreacted borate 2 (+22.3, s, ~8%). Further heating did not improve the yield of catecholborane.

EXAMPLE 9

Preparation of catecholborane from borate 2 and Lewis base-BH$_3$ in a solvent:

The procedure followed in all the solvents, such as tetrahydrofuran, hydrocarbon solvents with boiling point more than 50° C., dichloromethane and with various borane-Lewis bases, wherein the Lewis base could be a cyclic ether, a dialkyl sulfide or a tertiary amine, is the same. The following procedures are representative.

An oven-dried RB flask provided with a septum inlet, stirring bar and a reflux condenser was assembled hot and cooled to room temperature under a stream of nitrogen. The flask was charged with the borate 2 (17.31 g, 50 mmol) in dry toluene followed by borane-methyl sulfide (5.0 mL, 10.2 M, 51 mmol). The contents were slowly heated to 100° C. (bath temperature) maintaining the constant pressure of dry nitrogen. The progress of the reaction was followed by $^{11}$B NMR analysis of the reaction mixture. It showed the disappearance of the peak due to the borane-methyl sulfide complex (−20.4 ppm, q) and the appearance of a new peak due to catecholborane (+28.3 ppm, d, ~90%). The reaction mixture also showed some amount of unreacted borate 2 (+22.3, s, ~10%). Further refluxing did not improve the yield of catecholborane.

EXAMPLE 10

Preparation of catecholborane from borate 2 and N, N-diethylaniline-BH$_3$ in toluene An oven-dried RB flask provided with a septum inlet, stirring bar and a reflux condenser was assembled hot and cooled to room temperature under a stream of nitrogen. The flask was charged with the borate 2 (17.31 g, 50 mmol) in dry toluene followed by N,N-diethylaniline-BH$_3$ (8.32 g, 51 mmol). The contents were slowly heated to 70° C. (bath temperature) maintaining the constant pressure of dry nitrogen. The progress of the reaction was followed by $^{11}$B NMR analysis of the reaction mixture. It showed the disappearance of the peak due to the borane-N,N-diethylaniline complex (−11.8 ppm, q) and the appearance of a new peak due to catecholborane (+28.3 ppm, d, ~90%). The reaction mixture also showed some amount of unreacted borate 2 (+22.3, s, ~10%). Further refluxing did not improve the yield of catecholborane.

What is claimed is:

1. An improved process for the preparation of catecholborane comprising the reaction of tri-O-phenylene bis borate with diborane.

2. The process of claim 1 wherein tri-O-phenylene bis borate is reacted with diborane in a solvent inert to catecholborane and diborane.

3. A process for the preparation of catecholborane according to the claim 2, where in the solvent is selected from the group comprising di-, tri- or tetraglyme, or other solvents that does not react with diborane and catecholborane, such as hexadecane, tetralin, diphenyl ether etc.

4. An improved process for the preparation of catecholborane involving the reaction of tri-O-phenylene bis borate with a borane-Lewis base, complex without any solvent.

5. A process for the preparation of catecholborane according to the claim 4, wherein the Lewis base is selected from the group comprising cyclic ethers, such as tetrahydrofuran and tetrahydropyran, organic sulfides, such as dimethyl sulfide, diisoamyl sulfide and thioxane, tertiary amines, such as triethylamine, tert-butyldiethylamine, N,N-diethylaniline and N-ethyl-N-isopropylaniline.

6. An improved process for the preparation of catecholborane involving the reaction of tri-O-phenylene his borate with a selected Lewis base-borane complex in an appropriate solvent.

7. A process for the preparation of catecholborane according to the claim 6, wherein the solvent used is selected from the group comprising an ether, an aliphatic or aromatic halogenated hydrocarbons and an aliphatic or aromatic hydrocarbon with boiling points in the range of 50–300° C.

8. A process for the preparation of catecholborane according to the claim 6, wherein the Lewis base is selected from a cyclic ether, an organic sulfide, and a tertiary amine.

* * * * *